(12) United States Patent
Allen et al.

(10) Patent No.: US 11,019,922 B1
(45) Date of Patent: Jun. 1, 2021

(54) CHEMICAL UNIT FOR LOCKER

(71) Applicants: Sam Allen, Maypearl, TX (US); John Allen, Desoto, TX (US)

(72) Inventors: Sam Allen, Maypearl, TX (US); John Allen, Desoto, TX (US)

(*) Notice: Subject to any disclaimer, the term of this patent is extended or adjusted under 35 U.S.C. 154(b) by 0 days.

(21) Appl. No.: 16/838,620

(22) Filed: Apr. 2, 2020

Related U.S. Application Data

(63) Continuation-in-part of application No. 16/821,699, filed on Mar. 17, 2020, which is a continuation-in-part of application No. 16/429,895, filed on Jun. 3, 2019, now Pat. No. 10,640,910.

(51) Int. Cl.
| | |
|---|---|
| *F26B 25/06* | (2006.01) |
| *A47B 61/00* | (2006.01) |
| *F24F 3/16* | (2021.01) |
| *A61L 9/12* | (2006.01) |
| *F24F 8/24* | (2021.01) |

(52) U.S. Cl.
CPC .............. *A47B 61/00* (2013.01); *A61L 9/122* (2013.01); *F24F 3/16* (2013.01); *A61L 2209/11* (2013.01); *A61L 2209/15* (2013.01); *A61L 2209/16* (2013.01); *A61L 2209/212* (2013.01); *F24F 8/24* (2021.01)

(58) Field of Classification Search
CPC ... A47B 61/00; A61L 9/122; A61L 2209/212; A61L 2209/15; A61L 2209/16; A61L 2209/11; F24F 3/16; F24F 2003/1675; F26B 9/00
USPC .................. 34/235, 210, 201, 202, 209, 212
See application file for complete search history.

(56) References Cited

U.S. PATENT DOCUMENTS

| | | | |
|---|---|---|---|
| 5,369,892 A | 12/1994 | Dhaemers | |
| 8,756,827 B1 | 6/2014 | Calabro et al. | |
| 9,845,561 B2 | 12/2017 | Doyle et al. | |
| 10,612,846 B2* | 4/2020 | Allen | F26B 21/006 |
| 2007/0193058 A1 | 8/2007 | Zarembinski | |
| 2008/0256826 A1 | 10/2008 | Zarembinski | |
| 2018/0094855 A1 | 4/2018 | Allen | |
| 2018/0311396 A1* | 11/2018 | Lynn | A61L 2/202 |

(Continued)

FOREIGN PATENT DOCUMENTS

KR          20190006254 A  *  7/2017  ............... A61L 9/12

OTHER PUBLICATIONS

Publication dated Sep. 19, 2019 from corresponding U.S. Appl. No. 16/429,895.

(Continued)

*Primary Examiner* — John P McCormack
(74) *Attorney, Agent, or Firm* — James E. Walton

(57) ABSTRACT

A locker includes a pair of upstanding sidewalls, upper and lower horizontal panels, a plenum, and at least one compartment defined between the upstanding sidewalls. A chemical dispensing unit is disposed on or in the locker relative to the upper and lower horizontal panels, over and/or between the sidewalls. A first fan is disposed between the chemical dispensing unit and the plenum of the locker. The first fan pulls air and chemical into perforations formed in the locker to dispense the chemical throughout and in close proximity to the locker and remove dirty air. The first fan, or a second fan, draws clean air through the perforations of the locker. The dirty, chemical-integrated-air exits the locker room out an exhaust vent and is replaced by the clean air.

20 Claims, 15 Drawing Sheets

(56) References Cited

U.S. PATENT DOCUMENTS

| | | |
|---|---|---|
| 2019/0063763 A1* | 2/2019 | Kleinberger ............ A61L 2/022 |
| 2019/0284748 A1 | 9/2019 | Allen |
| 2019/0314540 A1* | 10/2019 | Andrews ................ G10K 11/00 |
| 2020/0010007 A1 | 1/2020 | Sanders |
| 2020/0138997 A1* | 5/2020 | De Sanctis ............. A61L 9/122 |

OTHER PUBLICATIONS

Office Action dated Jan. 14, 2020 from corresponding U.S. Appl. No. 16/429,895.
Amendment dated Feb. 7, 2020 from corresponding U.S. Appl. No. 16/429,895.
Final Office Action dated Feb. 19, 2020 ffrom corresponding U.S. Appl. No. 16/429,895.
Amendment After Final dated Feb. 25, 2020 from corresponding U.S. Appl. No. 16/429,895.
Notice of Allowance dated Mar. 9, 2020 from corresponding U.S. Appl. No. 16/429,895.

* cited by examiner

CHEMICAL UNIT FOR LOCKER

CROSS-REFERENCE TO RELATED APPLICATIONS

This application is a continuation-in-part of application Ser. No. 16/821,699, filed Mar. 17, 2020, titled "High-Speed Drying Unit for Locker;" which is a continuation-in-part of application Ser. No. 16/429,895, filed Jun. 3, 2019, titled "High-Speed Drying Unit for Locker;" which are all hereby incorporated by reference in their entirety for all purposes.

BACKGROUND

1. Field of the Invention

The present invention relates generally to improvements in lockers or storage cabinets used in athletic or sporting facilities, and more specifically to compartments of such lockers for storing wet and/or odorous equipment.

2. Description of Related Art

The aesthetics and utility of lockers or storage cabinets in "locker rooms" of athletic and sporting facilities of sports teams and country clubs, for example, have become a measure of the quality and prestige of such organizations and an increasingly important aspect of recruiting new team or club members. Modern lockers are a far cry from the simple wood or metal cabinets of the past.

Modern lockers incorporate storage for specific items of equipment, such as helmets and shoes, and features promoting comfort and luxury. There is a constant need for improvement in both functional and aesthetic aspects of such lockers, including the ability to store athletic or sporting equipment in ways that prolong their useful life.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
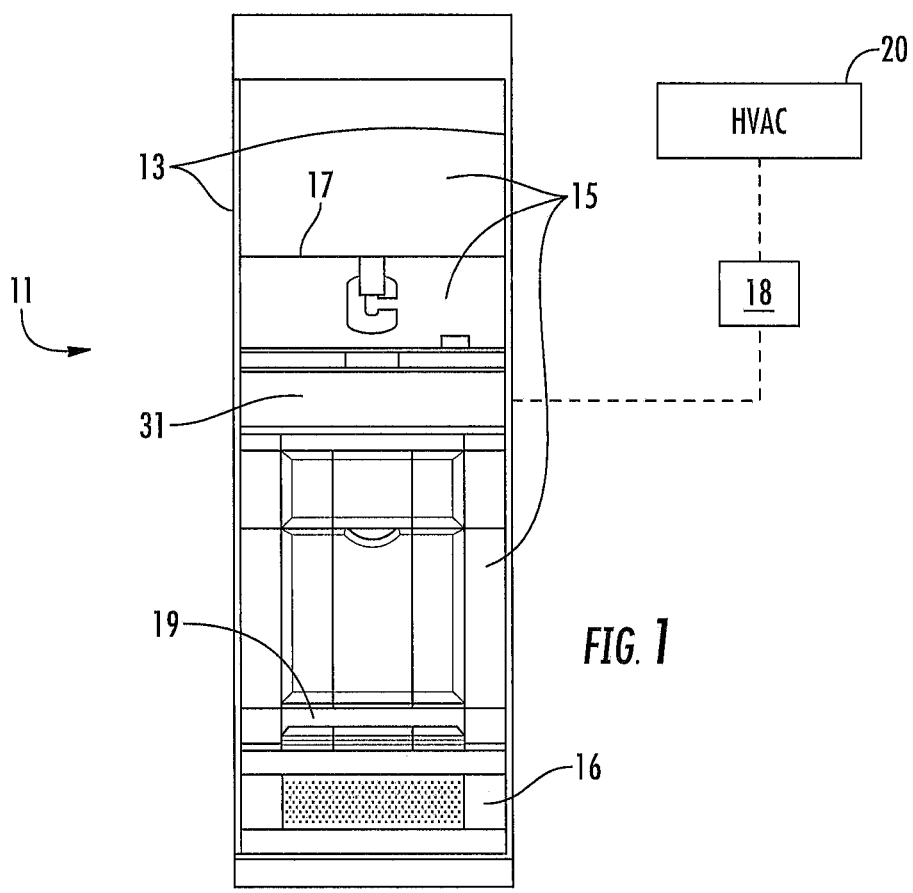
FIG. 1 is an elevation view of a locker having a high-speed drying unit according to the present application.
Figure 2A:
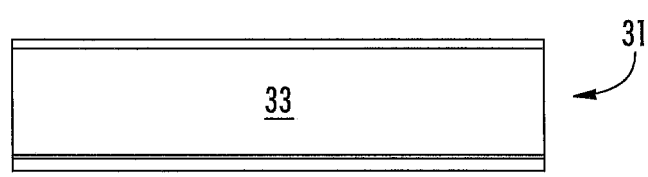
FIGS. 2A and 2B are enlarged elevation views of a drying unit of the locker of FIG. 1, with the door closed and opened, respectively.
Figure 2B:
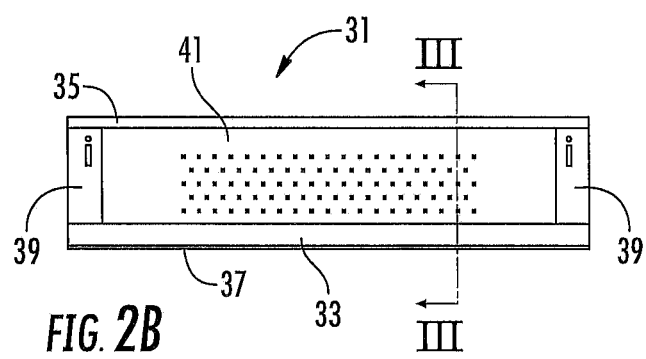
Figure 3:
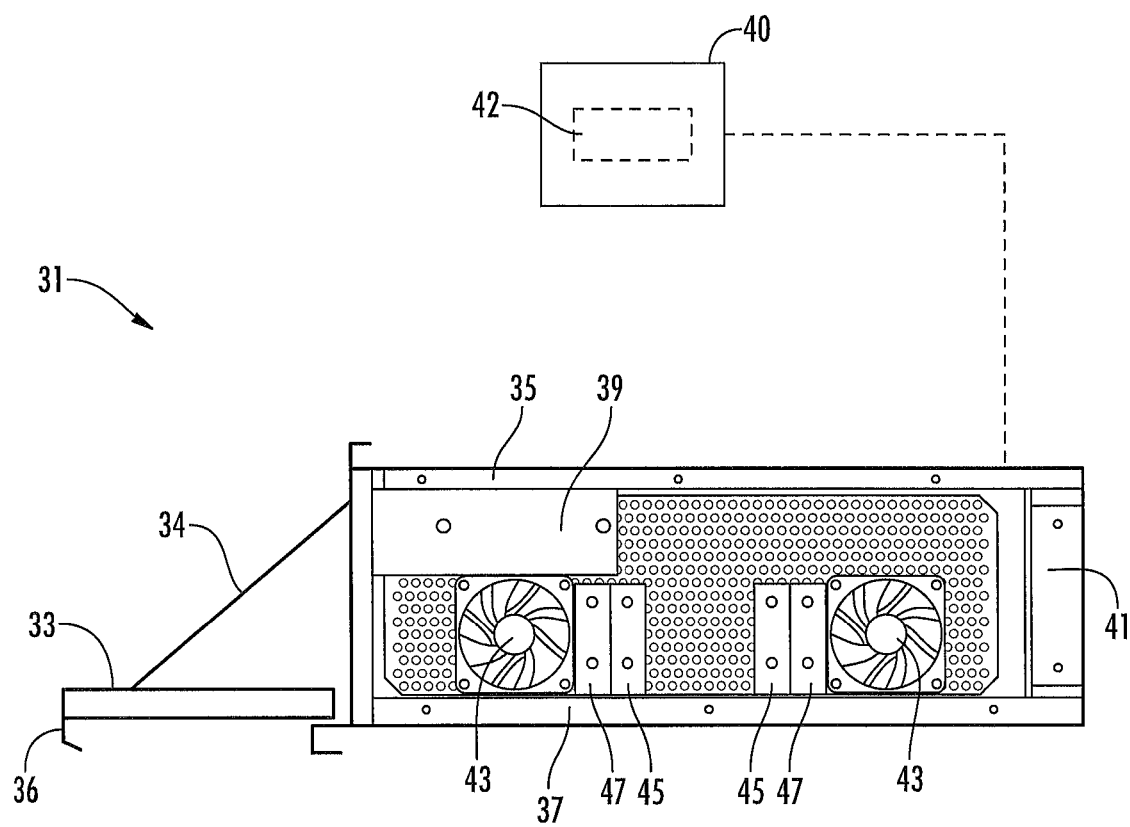
FIG. 3 is a side section view, taken along section line III-III of FIG. 2B.

While the assembly and method of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the locker, high-speed drying unit, and chemical unit of the present application are provided below. It will of course be appreciated that in the development of any actual embodiment, numerous implementation-specific decisions will be made to achieve the developer's specific goals, such as compliance with assembly-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

As used in conjunction with a drying unit, the term "high-speed" means a drying time associated with the function and capabilities of the drying unit, as described herein, that is less than or equal to seventy-five minutes for drying water-soaked equipment, including knee pads and cleats. As used in conjunction with a fan, the term means a fan rated at about 80 cubic feet per minute or more.

As used herein, the term "chemical dispensing unit" means an actuated device that has an inlet, an outlet, and a flow path, capable of delivering a chemical from a chemical chamber or a storage tank to the inlet, and from the inlet along the flow path to the outlet. The term also means an actuated device that has an inlet, an outlet, and a flow path, capable of converting a first chemical to a second chemical at the inlet, or from the inlet along the flow path and to the outlet. The mode of delivery includes pressure differentials created by pneumatic force, mechanical force, centripetal force, gravity, capillary effect, and combinations thereof. The mode of delivery may also include creating an electric differential, as with charged particles and ionic interactions. The mode of delivery may further include a diffusion reaction, or a dispersion of a highly concentrated substance to an area of lesser concentration. The dispersion rate is adjustable based on operational parameters of the drying unit, such as fan output, temperature readings from a thermometer or other temperature gauge, voltage input/output (I/O) readings, and combinations thereof. The dispersion rate may be further adjustable based on additional operational parameters and control variables, such as user input and settings, locker location, locker dimensions, drying unit dimensions, inlet and/or outlet dimensions, flow path dimensions, the mode of delivery, and combinations thereof.

As used in conjunction with a chemical dispensing unit, the term "chemical" means any gas, emulsion, element, molecule, group of molecules, or fluid in aerosol or nebulized form, capable of being airborne to travel to various compartments of a locker. The chemical preferably has deodorizing, disinfecting, neutralizing, or similar beneficial properties. However, in some contexts, the term "chemical" is also used to refer to odorous, unbeneficial substances, such as bacteria, that may be generated due to stagnant water and moisture from athletic equipment stored in a locker. These "unbeneficial substances" are generally referred to herein as odorous chemicals.

As used in conjunction with a chemical unit, the term "integrated" means a chemical unit associated with the function, capabilities, and/or proximal location of one or more lockers, as described herein. The integrated chemical unit is attached, connected, fluidly coupled, and/or secured on, in, or in close proximity to a compartment associated with the one or more lockers. However, the integrated chemical unit may have sufficient capacity to be able to apply chemical to the air surrounding multiple lockers, such that a group of lockers has only one integrated chemical unit attached to a single locker of the group, which is configured to apply chemical for the entire group of lockers. As used in conjunction with a fan, the term means a fan abutting, adjacent, or in close proximity to the integrated chemical unit. Such fans are rated at about 20-80 cubic feet per minute or more.

As used herein, the term "heating element" means a mechanical, chemical, or electrical device capable of creating a temperature differential. The term encompasses a heater that uses resistor heating coils or elements, a furnace that uses petroleum or natural gas, or a thermoelectric unit that relies on the Peltier Effect. Other similar thermodynamic devices will be recognized and are encompassed by the term. As used in conjunction with the drying unit, the term means a small-scale device that is smaller in scale than an HVAC furnace, such as an electrical resistor heater, a Peltier Unit, or a thermodynamic device that is dimensioned to be housed within a removable drying unit. The removable drying unit itself being dimensioned to fit within a compartment of a locker.

Referring now to FIG. 1 in the drawings, a locker 11 according to the present application is illustrated. As can be seen, locker 11 comprises a pair of upstanding sidewalls 13 that generally define the extent of locker 11. Sidewalls 13 may be connected at the rear by a rear wall, at the top by a top wall, and at the bottom by a bottom wall. It will be appreciated that the rear wall, the top wall, and the bottom wall may be formed of multiple components parts, each of which may perform additional functions other than merely forming an enclosure, such as ventilation plenums, interconnecting surfaces, ventilation conduits, electrical conduits, etc. Each locker may be installed adjacent to another, similar or identical locker, with its rear against a wall, and its front facing the interior of the locker room.

Between sidewalls 13 of locker 11, a plurality of compartments 15 are defined by dividers 17 that may include vertical panels parallel to sidewalls 13, or shelves or other horizontally extending surfaces, panels, or platforms that serve to connect sidewalls 13 and lend rigidity and strength to locker 11, in addition to forming compartments 15. Each compartment 15 may be sized and otherwise configured for storage of clothing, sporting equipment, or other items, and may include doors, ventilation grills, sliding components, tilting components, equipment racks, and equipment holders, any of which may be lockable. Locker 11 may also include a generally horizontal seat 19, which sits atop a "footlocker" or lowermost footlocker compartment 16, which may be forward of the remainder of locker 11, and which may form a door to the footlocker compartment 16.

In at least one embodiment, locker 11 is in fluid communication with a forced-air ventilation system 18. The forced-air ventilation system may be connected to an HVAC 20 of the locker room, or of the building in which the locker 11 is disposed, where the HVAC includes a furnace.

Referring now also to FIGS. 2A, 2B, and 3 in the drawings, included among the various compartments 15 of locker 11 may be a high-speed drying unit 31. According to a preferred embodiment of the present application, drying unit 31 may be a full- or partial-width, rectangular, or otherwise configured, compartment adapted particularly for the storage and high-speed drying of wet equipment and/or clothing. Drying unit 31 may be integrally installed into locker 11, or may be installed as a stand-alone unit that can be quickly and easily removed and replaced for servicing, maintenance, or interchangeability. Drying unit 31 is preferably provided with a door 33 that may be accessed from the front of locker 11, and that is hinged at a lower extent, so that, in the open position (FIGS. 2B and 3), the full width and height of drying unit 31 is opened and accessible. A handle 36 may be provided at the upper extent, or other convenient location, of door 33 and preferably is of bent stainless steel or aluminum, but may be of any configuration. A door support mechanism 34, such as one or more cables, a knife hinge, a damper, and/or a support strut, may be provided and coupled to door 33 to prevent over-travel and support. Door support mechanism 34 may include counterweight features to assist with opening and closing door 33, and may include pneumatic cylinders or other components to provide a soft-close element to drying unit 31.

Upper 35 and lower 37 shelves or horizontal dividers are preferably formed of corrosion-resistant metallic or polymer material (preferably stainless steel) and are hollow and open at least the forward or front ends and serve as air intakes. Shelves 35 and 37 extend at least partially between sidewalls 13 and are in fluid communication with right and left compartment sidewalls 39, which may be formed of at least partially perforated metallic or polymer material, again preferably stainless steel, and may be hollow structures. Compartment sidewalls 39 are just interior of locker sidewalls 13 and extend between and connect shelves 35 and 37. In a similar fashion, a rear wall 41 may be at least partially perforated and formed or metallic or polymeric material to resist corrosion.

As shown in FIG. 3, at least one, and preferably two, high-speed ventilation fans 43 may be provided in each (right and left) sidewall 39. Fans 43 preferably may be Delta AFB812EHE (available from Delta Electronics (Americas) Ltd., 46101 Fremont Blvd., Fremont, Calif. 94538) 80 mm fans rated at about 80 cubic feet per minute capacity and are configured to direct forced air to the interior of drying unit 31. Other fan sizes and capacities may be desired depending upon the volume, size, and shape of drying unit 31, depending upon the amount of time desired to dry the clothes and/or equipment placed in drying unit 31, and/or depending upon other factors, such as the particular equipment to be dried, ambient conditions, etc. It will be appreciated that this unique high-speed drying system has a significantly higher capacity than conventional ventilation systems in lockers.

The unique functionality and capacity of drying unit 31 is best understood by an actual example performed with a working prototype of drying unit 31. In the example, a pair of adult cleats were filled with water and the water was allowed to soak in for two minutes. After two minutes, the remaining water was poured out of the cleats. In addition, a pair of knee braces were dunked under water for several seconds and then removed from the water. Then, the water-soaked cleats and the water-soaked knee braces were placed in drying unit 31. Drying unit 31 was turned on and the cleats and the knee braces were dry in about seventy-five minutes. This example was performed without the use of the optional heating elements described below.

A control system 40 connected to the high-speed drying unit 31 includes programmable logic or executable instructions 42 for setting temperature parameters, control limits, variable speed fan motor inputs and/or voltages, or combinations thereof. The control system 40 includes, but is not limited to, a processor, non-volatile memory, field programmable devices including programmable ROM (PROM), electrically erasable ROM (EEPROM), field programmable logic arrays (FPLA), a programmable array logic device (PAL®), a complex programmable logic device (CPLD), a field-programmable gate array (FPGA), and combinations thereof.

Locker 11 may include a forced-air ventilation system, and the forced-air ventilation system may be connected to an HVAC system for the locker room, so that the "dirty" air being circulated throughout locker 11 may be vented and/or filtered outside of the locker room. Drying unit 31 may be separate from such forced-air ventilation system contain in locker 11, or may be integrated with such forced-air ventilation system of locker 11. Indeed, it may be desirable to exhaust the air from drying unit 31 to an external location to assist in eliminating any odor contained within drying unit 31 and/or the items being dried. Thus, drying unit 31 may include conduits and adapters for attachment to the forced-air ventilation system and/or the HVAC system.

Drying unit 31 may include one or more heating elements 45 to assist in the high-speed drying of the clothing and/or equipment placed in drying unit 31. The heating elements 45 selectively heat the air that is circulated by fans 43, thereby accelerating the time required to dry the equipment and/or clothing. In addition, drying unit 31 may include one or more chemical dispensing units 47 for selectively dispensing chemicals, such as detergents, deodorants, anti-bacterial chemicals, anti-static substances, etc. during the operation of drying unit 31. The heating elements 45 and the chemical dispensing units 47 are preferably disposed within void spaces in upper and lower shelves 35 and 37, side walls 39, and/or rear wall 41 of drying unit 31. It will be appreciated that the fans 43, the heating elements 45, and/or the chemical dispensing units 47 may be controlled by a specialized microprocessor-controlled computerized control system and/or computer network that may be selectively programmed to control the operational parameters and maintenance of drying unit 31. In this manner, multiple drying units 31 over multiple lockers 11 may be networked together to perform the efficient operation of drying units 31. It will be appreciated that the heating elements 45 may be in communication with a centralized source of heat, such as a main gas or electric heater, boiler, or other heat source, where the heat is distributed to the individual lockers 11. Similarly, the chemical dispensing units 47 may be in communication with a centralized source of chemicals, such as tank or reservoir, where the chemicals are distributed to the individual lockers.

In operation, wet clothing and/or equipment may be inserted into drying unit 31. Fans 43 may be energized or turned on by a manual switch or automatically via the control system. The control system may include an optical or other type of sensor that detects the presence of items in drying unit 31 and energizes fans 43 only while items are present and require drying. Fans 43 may alternatively run "full-time" or on a timer on a specific, predetermined schedule, for example, at night, or for two hours after events or practices are scheduled to end.

Fans 43, when energized, draw air from the exterior of locker 11 through hollow shelves or panels 35 and 37, into sidewalls 39, and into the interior of compartment 31. Shelves or panels 35 and 37 and compartment sidewalls 39 act as intakes and ducts for the air moved by fans 43. The circulating, forced air assists in drying the items in compartment 31. Air may be exhausted or diffused through perforated rear panel 41, either to the atmosphere external to locker 11, or to the plenum of a forced-air ventilation system as described in commonly invented U.S. application Ser. No. 15/897,875, filed Feb. 15, 2018, and Ser. No. 15/823,073, filed Dec. 5, 2017, which are incorporated herein by reference for all purposes. The heating elements and/or the chemical dispensers may be selectively utilized during the drying process.

Fans 43, heating element 45, and chemical dispensing unit 47 are connected in a linear fashion. In this configuration, the air drawn from the exterior of locker 11 passes through the chemical dispensing unit 47, then is heated by the heating element 45, and finally emitted into a chamber of the drying unit 31.

Figure 4A:
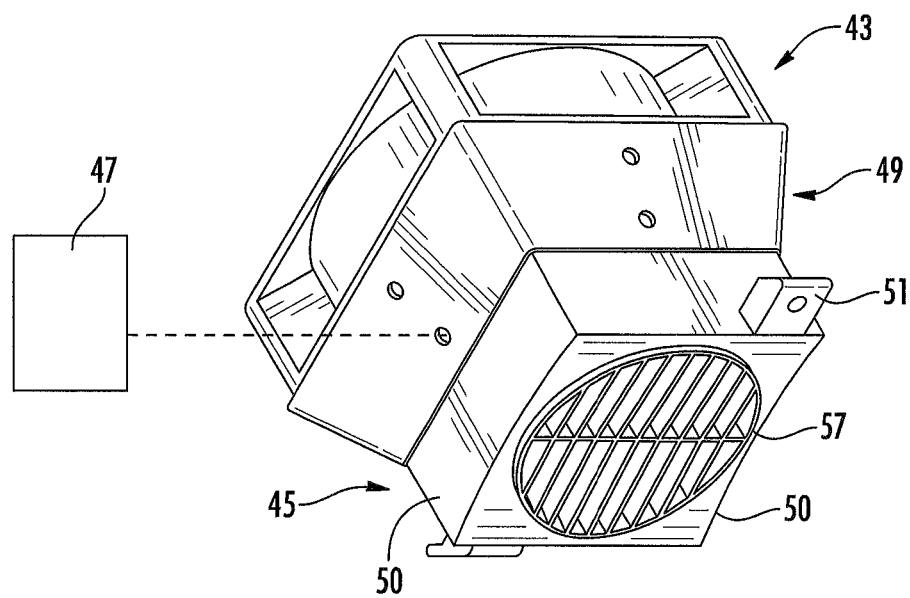
FIGS. 4A through 4C are perspective, side, and top views of a heating element of a high-speed drying unit of the locker of FIG. 1.
Figure 4B:
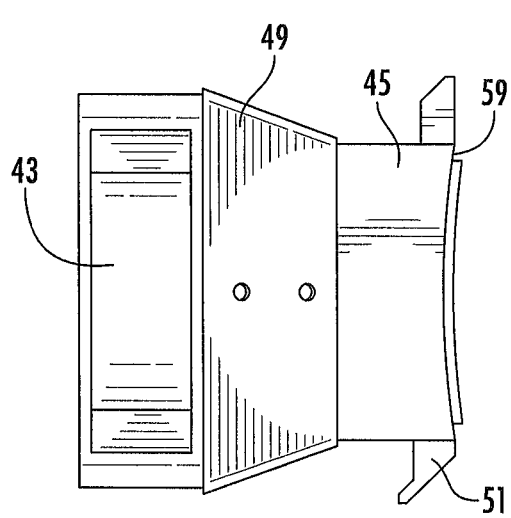
Figure 4C:
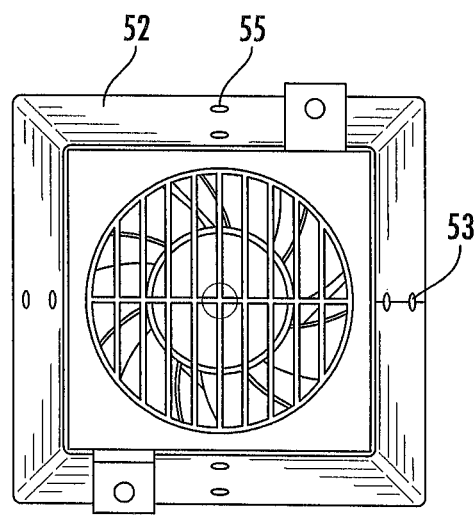

As shown in FIGS. 4A through 4C, an alternative embodiment includes a duct 49 connecting blower fan 43 to the heating element 45. Heating element 45 is at least one of a resistive heater, a Peltier Unit, or a furnace of an HVAC unit, and includes a pair of sidewalls 50 and one or more mounts 51. The one or more mounts 51 are flat, angled, or a combination thereof, depending on an attachment location relative to locker 11. Duct 49 is preferably a two-piece duct made from flat pattern or sheet metal, including a duct wall 52 and a connector 53 to connect a seam of the duct wall 52.

Duct 49 includes one or more apertures 55. The one or more apertures 55 may be used for ventilation, attachment, or for dispersing chemicals when a chemical dispensing unit 47 is located within the duct 49. The blower fan 43 is either a positive pressure or a negative pressure fan, however, in this embodiment the locker 11 uses a positive pressure fan. In other embodiments, duct 49 includes additional components, such as a plenum chamber, a wall stack, a collar, an angle stack boot, an elbow, and combinations thereof. The connector 53 includes, but is not limited to, a rivet, a weld, a self-tapping screw, a barrel clamp, gorelock, sealant, and combinations thereof.

The heating element 45 includes an air diffuser 57, including a grille, a grate, an air diffuser, or a series of apertures formed in a face plate. In positive pressure configurations, the air diffuser 57 is attached to an end 59 of the heating element 45 that is disposed in a wall or a shelf of the drying unit 31, or a wall or a shelf of the locker 11.

Figure 5A:
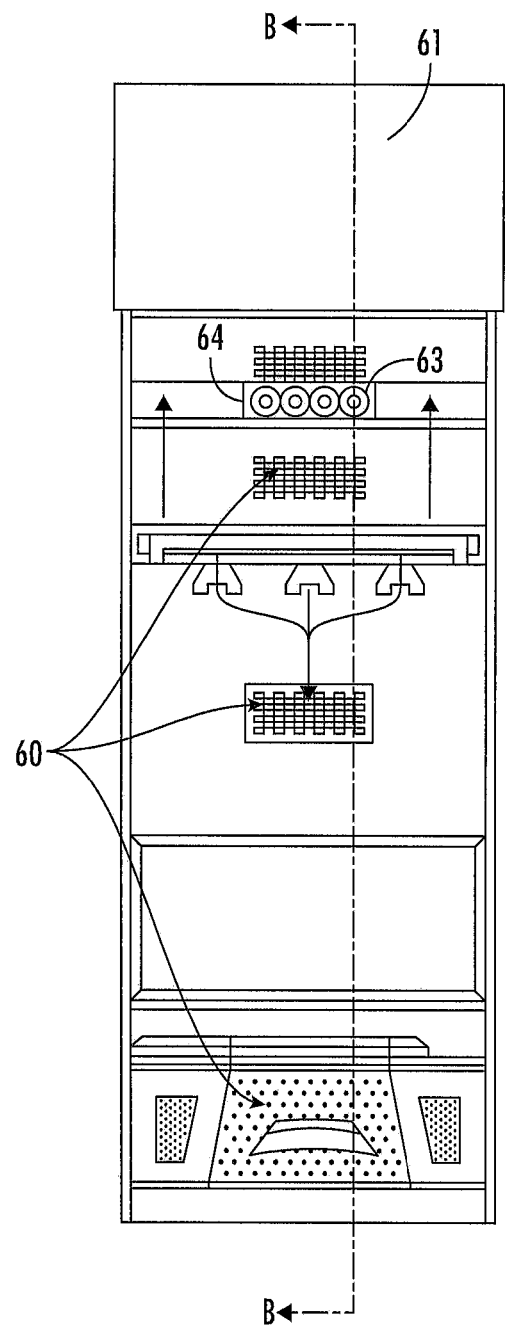
FIG. 5A is a front elevation view of a locker having a chemical unit according to the present application.

Referring now to FIG. 5A in the drawings, an elevation view of a locker 61 having an integrated chemical dispensing unit 63 is illustrated. The integrated chemical dispensing unit 63 uses one or more integrated fans 64 to interact with air flow, adds a chemical to the air flow, and ejects the chemical and air near to locker 61 to sterilize, deodorize, and/or displace bacteria and odorous chemicals emitted from equipment stored in the locker 61. The chemical-integrated air 60 is pulled to various portions and/or compartments of the locker 61. Preferably, the chemical comprises ozone, $O_3$, which may be formed from peroxide radicals, a decomposition reaction involving nascent oxygen, a photochemical reaction, ultra violet (UV) light, and combinations thereof. Alternatively, the chemical comprises ionized particles, electronically charged particles, deodorizing substances, such as hydroxylpropyl beta-cyclodextrin, and combinations thereof.

Figure 5B:
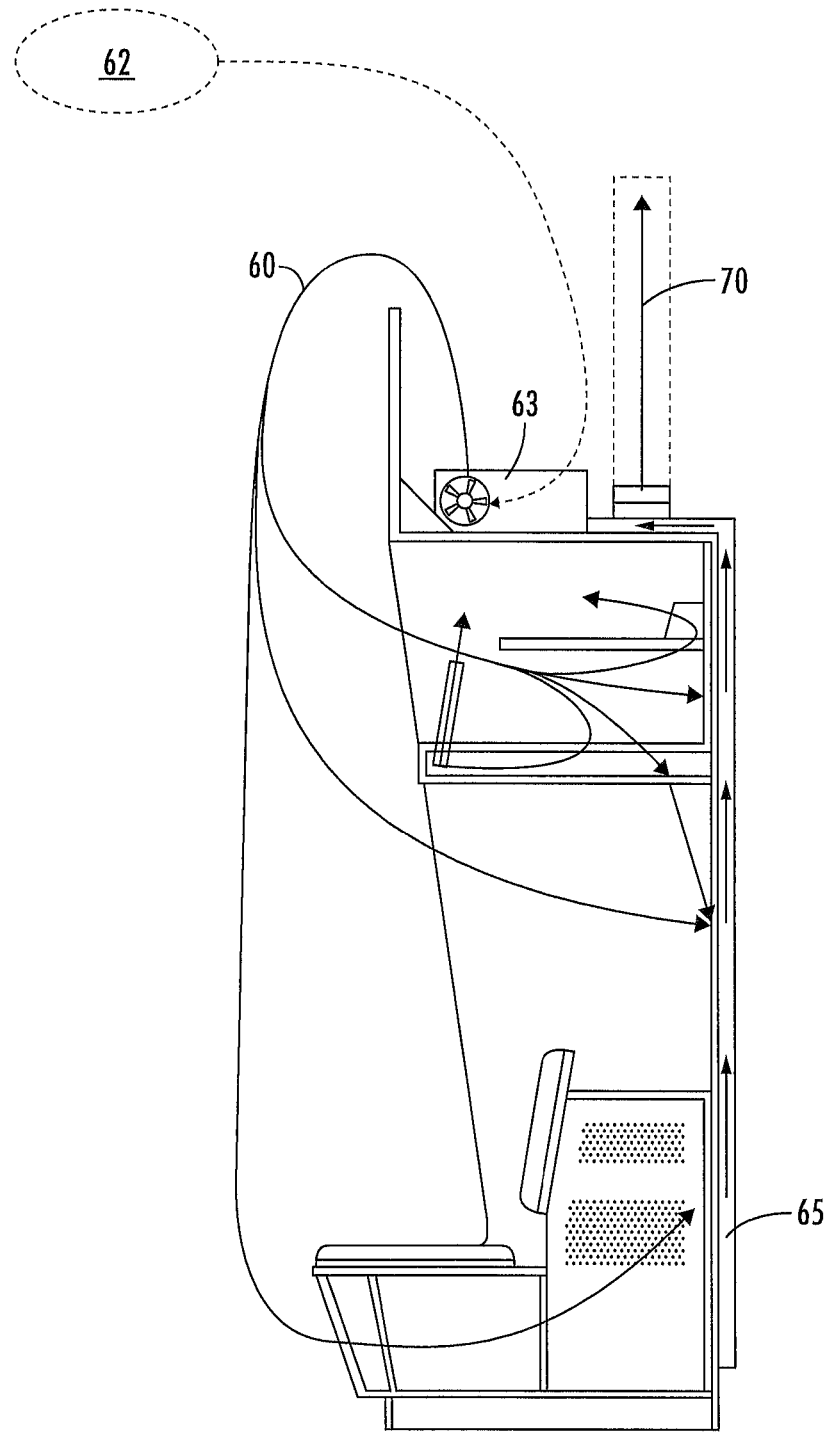
FIG. 5B is a section view of the locker of FIG. 1A taken along Section Line B according to the present application.

Referring now to FIG. 5B in the drawings, preferably the chemical dispensing unit is an ozone generator 63 capable of pulling room or ambient air 62 into the chemical dispensing unit, converting oxygen in the air to $O_3$, and then ejecting the ozone-integrated-air over and in front of the locker 61. The locker 61 is equipped with multiple fans to pull the ozone-integrated-air into the drying chambers, compartments, and equipment storage spaces of the locker 61, and then into a plenum 65.

Figure 5C:
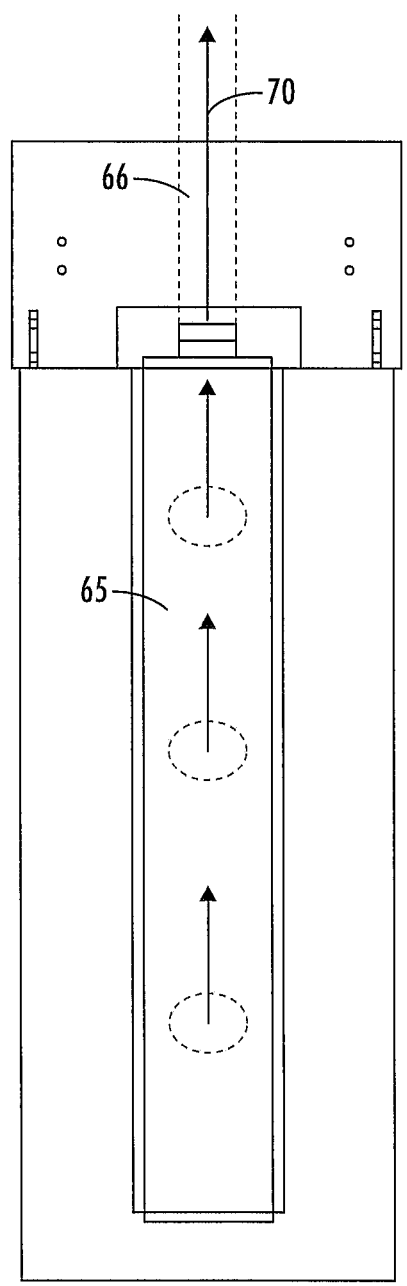
FIG. 5C is a back view of the locker of FIG. 1A according to the present application.

Referring now to FIG. 5C in the drawings, the plenum 65 is used to channel the dirty, ozone-integrated-air 70 out of the locker and into an exhaust vent 66 or duct system associated with the locker room. The exhaust vent 66 or duct system may include one or more UV sources, catalyst sources, humidifiers, radicals, and combinations thereof, spaced along the vent or duct system in order to convert the ozone in the exhaust to $O_2$. The radicals include, but are not limited to, chlorine (Cl), hydroxyl (OH), nitric oxide (NO), and bromine (Br).

Figure 6A:
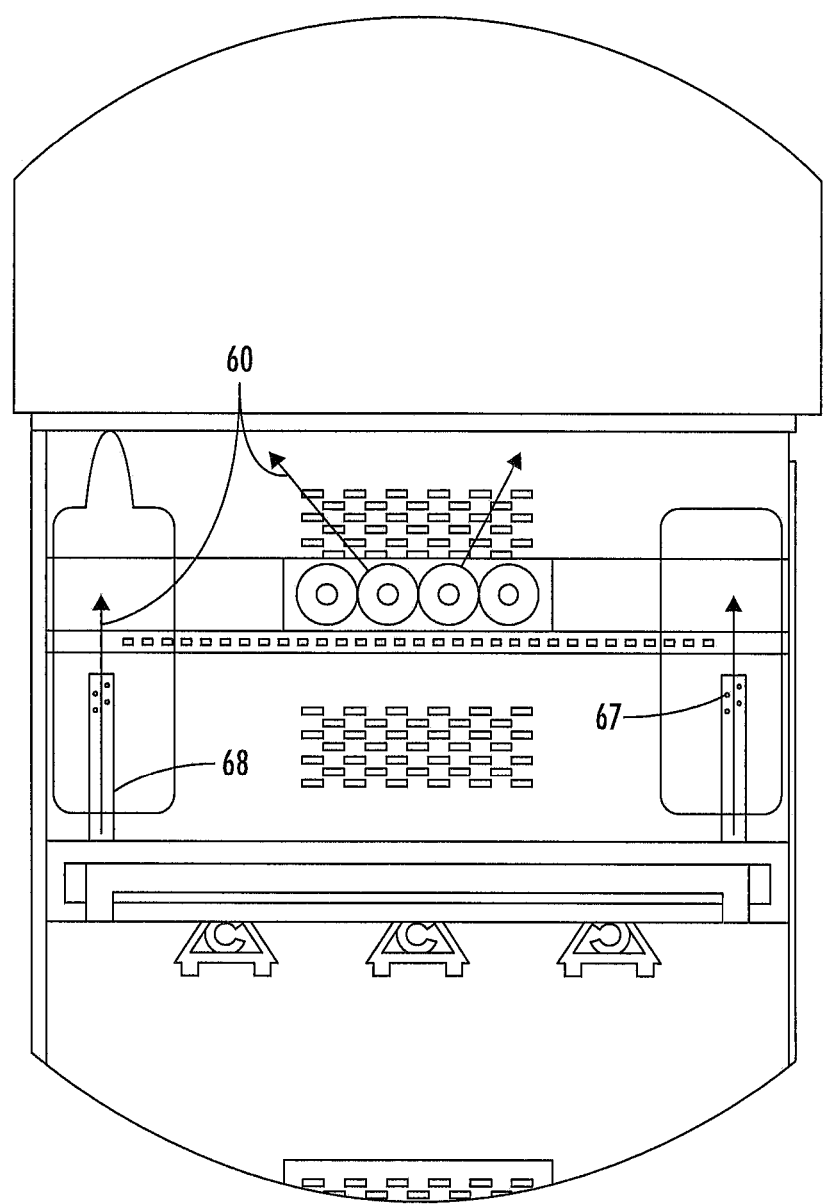
FIG. 6A is an enlarged front elevation view of the locker of FIG. 1A, depicting chemical dispersion and air flow according to the present application.

Referring now also to FIG. 6A in the drawings, dispensing apertures 67 are formed in a grate, an equipment rack 68, a locker sidewall or shelf, and combinations thereof. The apertures 67 are preferably oblong, allowing air to pass through, but not unwanted objects, such as keys, fingers, clothing, etc., but they may also be of any size and dimension. Apertures 67 are formed to receive and dispense a chemical, such as ozone, into and throughout one or more compartments of the locker 61.

Figure 6B:
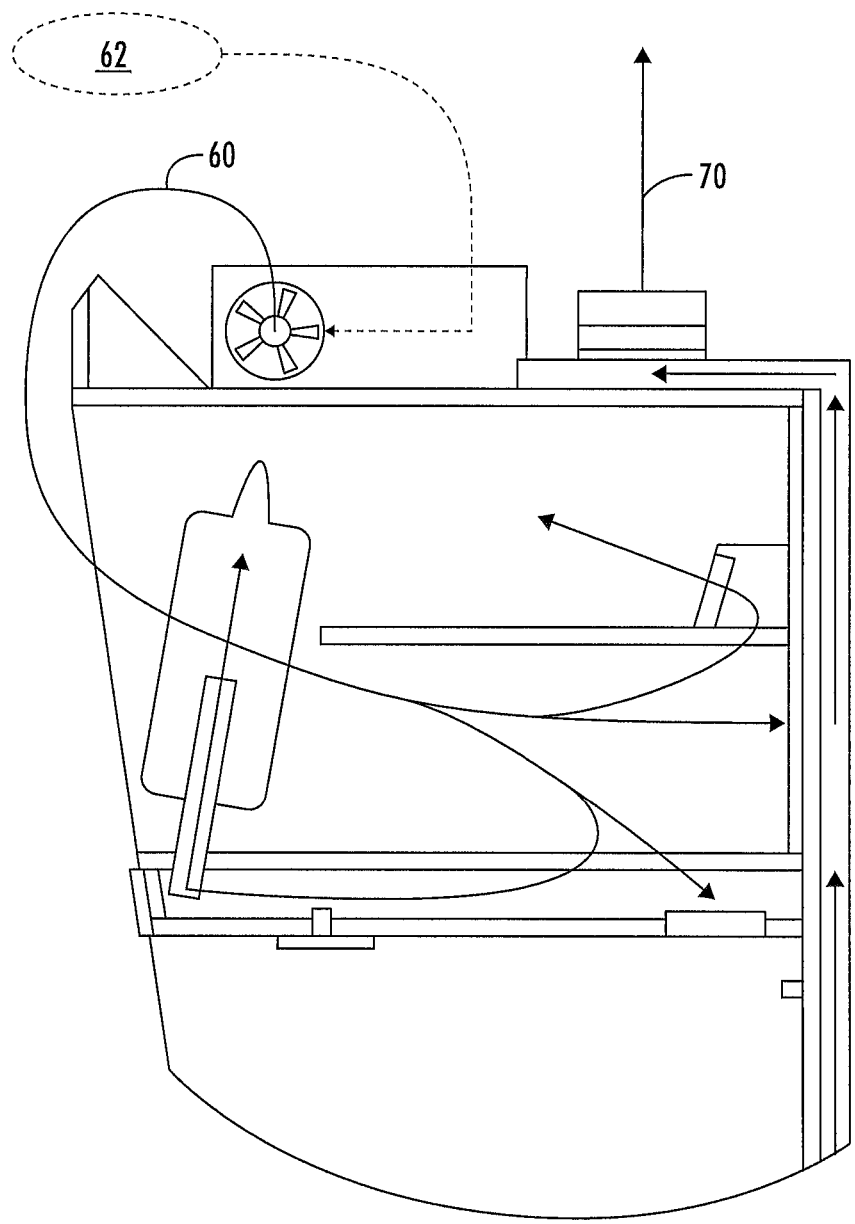
FIG. 6B is an enlarged section view of the locker of FIG. 1A, depicting chemical dispersion and air flow according to the present application.
Figure 6C:
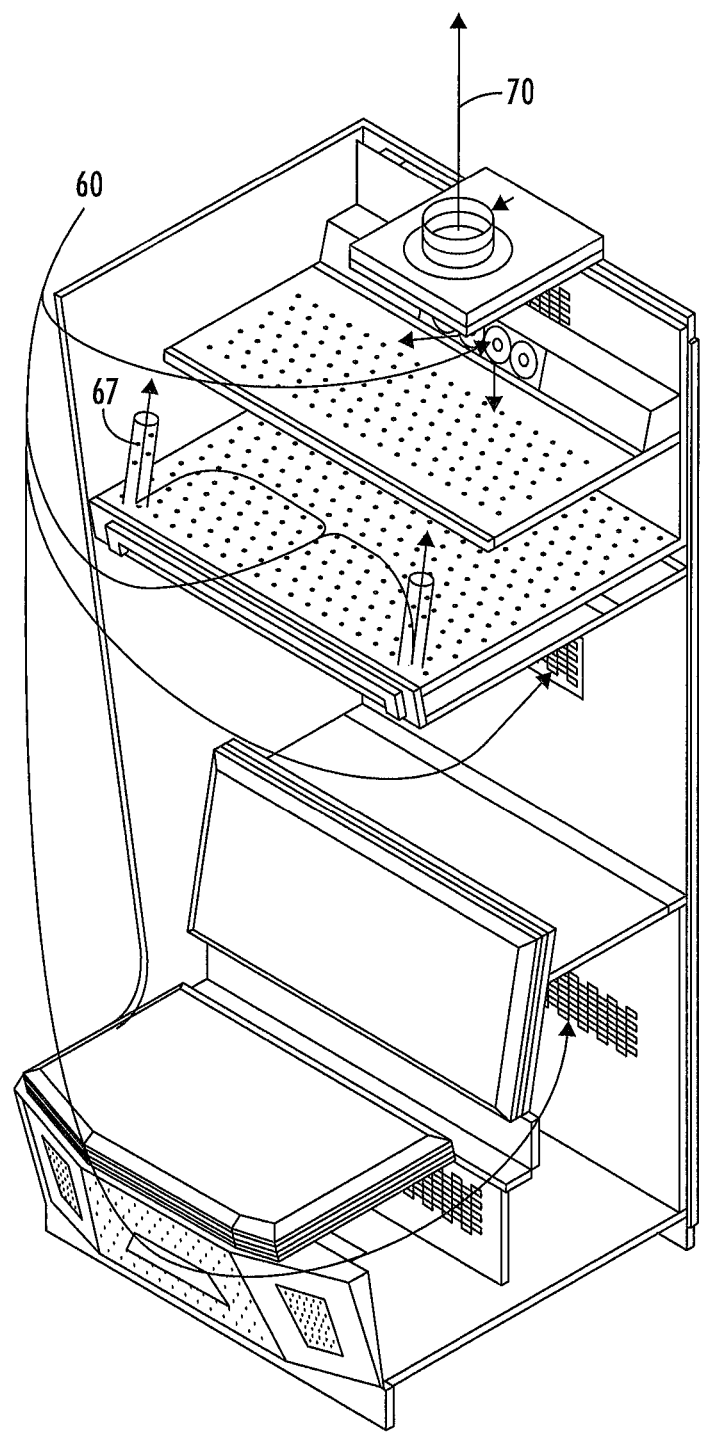
FIG. 6C is a perspective view of the locker of FIG. 1A, depicting chemical dispersion and dirty air flow according to the present application.

Referring now also to FIG. 6B in the drawings, a section view of the locker 61 is illustrated to depict ozone-integrated-air flow. Due to one or more integrated fans 64 disposed throughout the locker 61, the ozone-integrated-air is pulled into compartments and circulated throughout portions of the locker 61 to deodorize, decontaminate, and disperse bacteria and odors associated with equipment stored in the locker. More chemical pathways 69 are visible in the perspective view depicted in FIG. 6C. In this embodiment, the ozone-integrated-air in the locker room is completely replaced by fresh air. For example, a 1,500 square foot room, having 10-foot high walls has a volume of 15,000 $ft^3$. Thus, the time at which the locker room is completely filled with fresh air again depends on the number of chemical dispensing units used (which depends on the size of the room), a desired number of "air changes", the amount of ozone generated by each dispensing unit, how long the dispensing units emitted ozone into the room (depending on size of room as well as an amount of odor and/or bacteria detected), and the capacity of the exhaust and/or circulation fans. Preferably, six to nine ozone generators are used to produce a combined output of 90 g/hour of ozone. Each unit is connected to a fan rated at about 80 CFM. The units are operated for four to eight hours, or for a more extensive odor, 6-8 hours. A minimum of four hours are provided prior to reentry into the locker room.

Figure 7A:
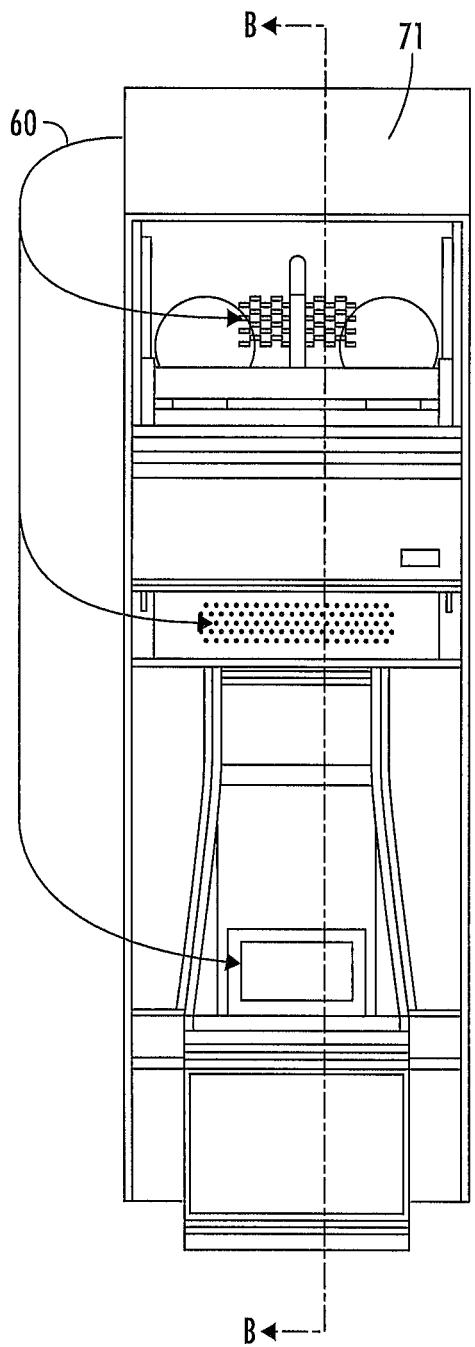
FIG. 7A is a front elevation view of an alternative embodiment of a locker having a chemical unit according to the present application.

Referring now to FIG. 7A in the drawings, a front elevation view of a locker 71 having an integrated chemical dispensing unit 73 is illustrated. The chemical dispensing unit 73 uses one or more induction fans 74 to recycle and/or re-circulate air flow and a chemical additive to sterilize, deodorize, and/or displace bacteria and odorous chemicals emitted from equipment stored in the locker 61. The chemical dispensing unit is configured to measure a concentration of bacteria, odor, and contaminants within the recirculated air 80 to determine how much longer the chemical dispensing units will inject chemicals into the air. This determination will also affect how long the exhaust fans and circulation fans will continue to run.

Figure 7B:
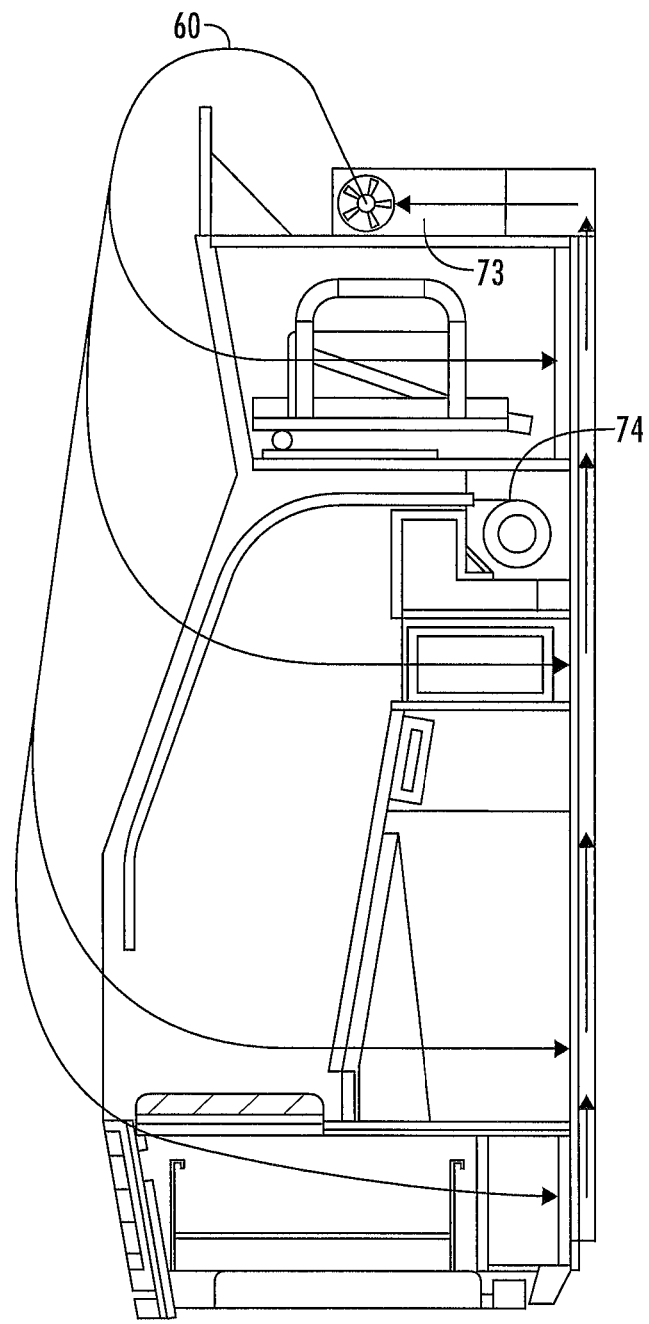
FIG. 7B is a section view of the locker of FIG. 3A taken along Section Line A according to the present application.

Referring now to FIG. 7B in the drawings, preferably the chemical dispensing unit 73 is an ozone generator capable of pulling dirty air, and/or ozone-integrated-air, into the chemical dispensing unit 73, measuring chemical concentration levels and/or odorous chemical concentration levels, and then ejecting the ozone-integrated-air in close proximity to the locker 71. The locker 71 is equipped with multiple circulation fans to re-circulate the ozone-integrated-air throughout the drying chambers, compartments, and equipment storage spaces of the locker 71.

Figure 7C:
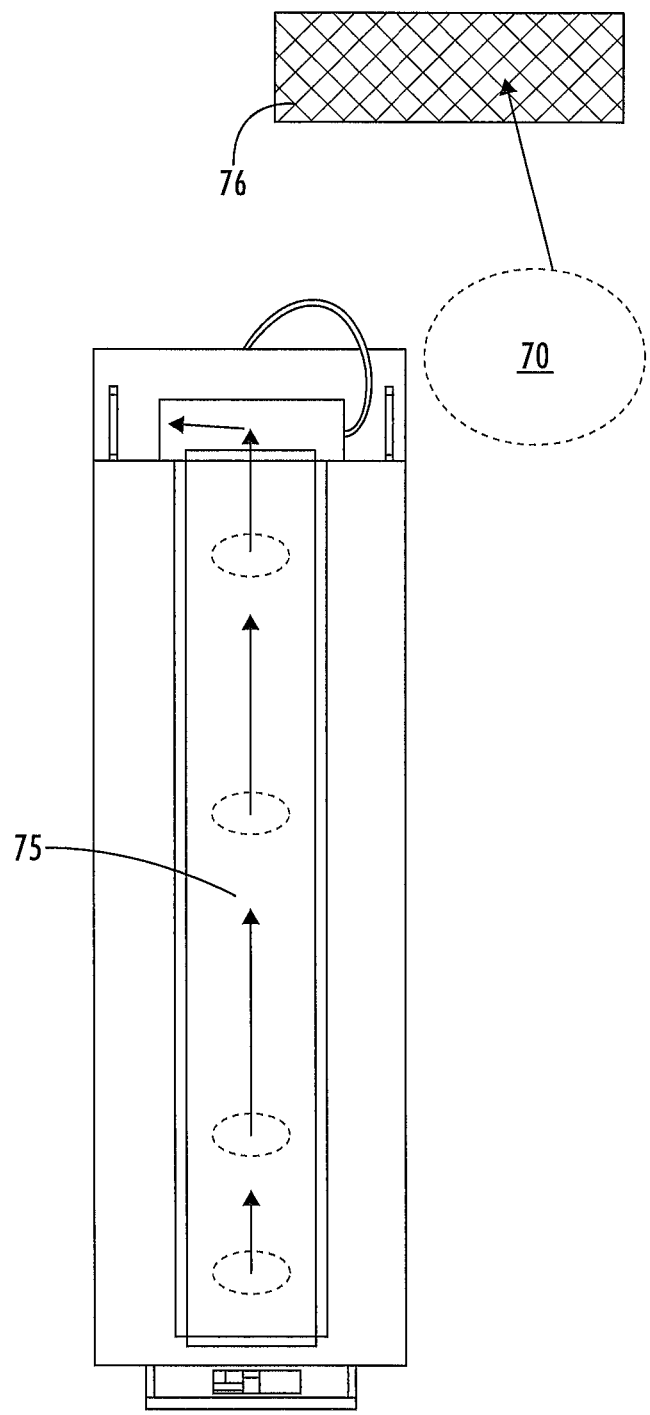
FIG. 7C is a back view of the locker of FIG. 7A according to the present application.

Referring now to FIG. 7C in the drawings, a plenum 75 is used to re-circulate ozone-integrated-air to the ozone generator 73 and throughout locker 71. An HVAC duct or vent 76 is used to vent the dirty air out of the locker room and into an exhaust vent or duct system associated with the locker room. The exhaust vent or duct system may include one or more UV sources, catalyst sources, radicals, and combinations thereof, spaced along the vent or duct system in order to convert the ozone in the exhaust to O2. The radicals include, but are not limited to, chlorine (Cl), hydroxyl (OH), nitric oxide (NO), and bromine (Br).

Figures 8A, 8B:
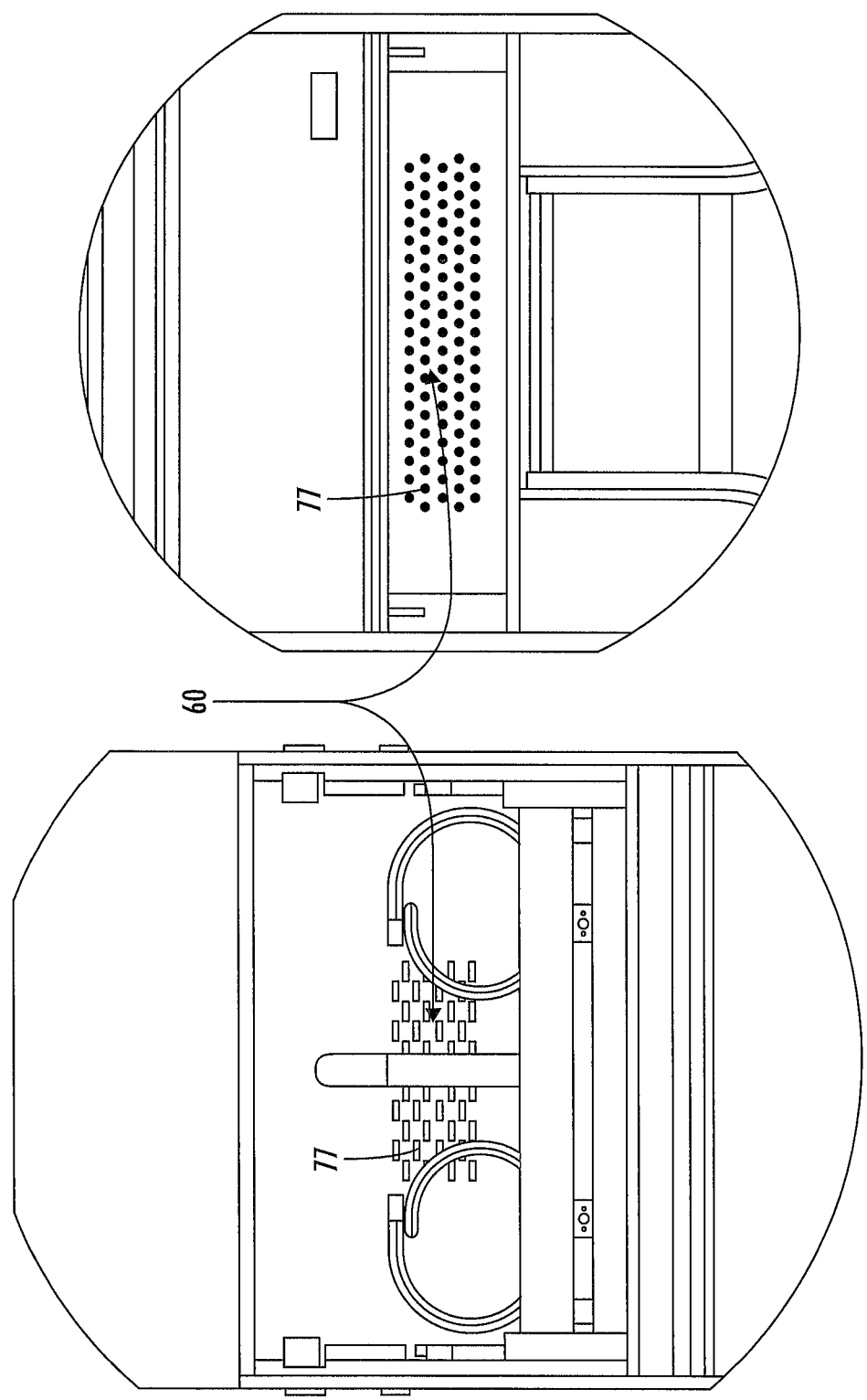
FIG. 8A is an enlarged elevation view of the locker of FIG. 7A, depicting chemical dispersion according to the present application.
FIG. 8B is an enlarged mid-section view of the locker of FIG. 7A, depicting chemical dispersion and air flow according to the present application.

Referring now also to FIGS. 8A and 8B in the drawings, dispensing apertures 77 are formed in a grate, an equipment rack, a locker sidewall or shelf, and/or combinations thereof as O3 and other chemical entry/re-circulation points. The apertures 77 are preferably circular, allowing air to pass through, but not unwanted objects, such as keys, fingers, clothing, etc., but they may also be of any size and dimension. Apertures 77 are formed to first receive a chemical and then receive the re-circulated chemical, such as ozone, dispersing the chemical throughout one or more compartments of the locker 71, such as a shoe compartment.

Figure 8C:
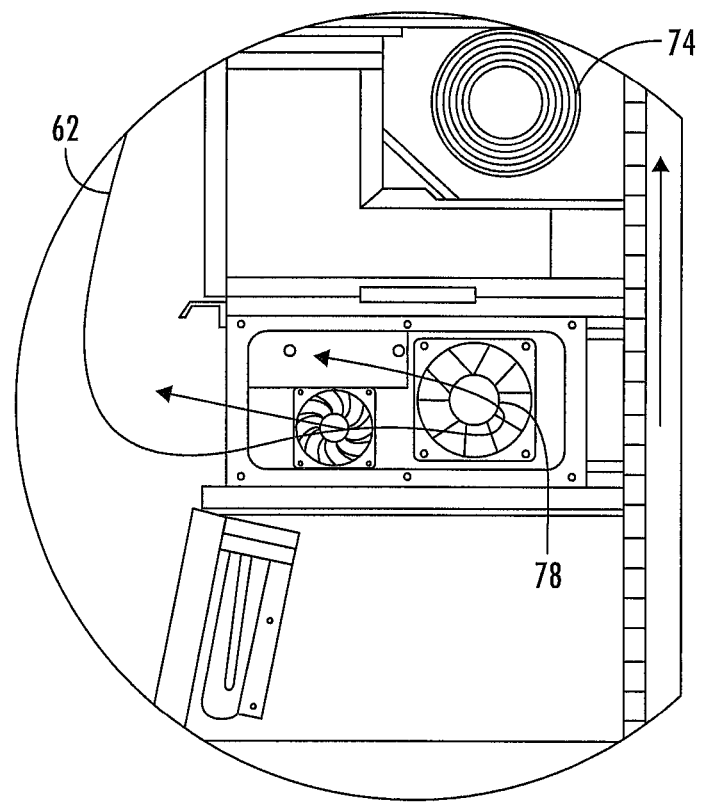
FIG. 8C is an enlarged section view of the locker of FIG. 3A, depicting chemical dispersion and dirty air flow according to the present application.
Figure 8D:
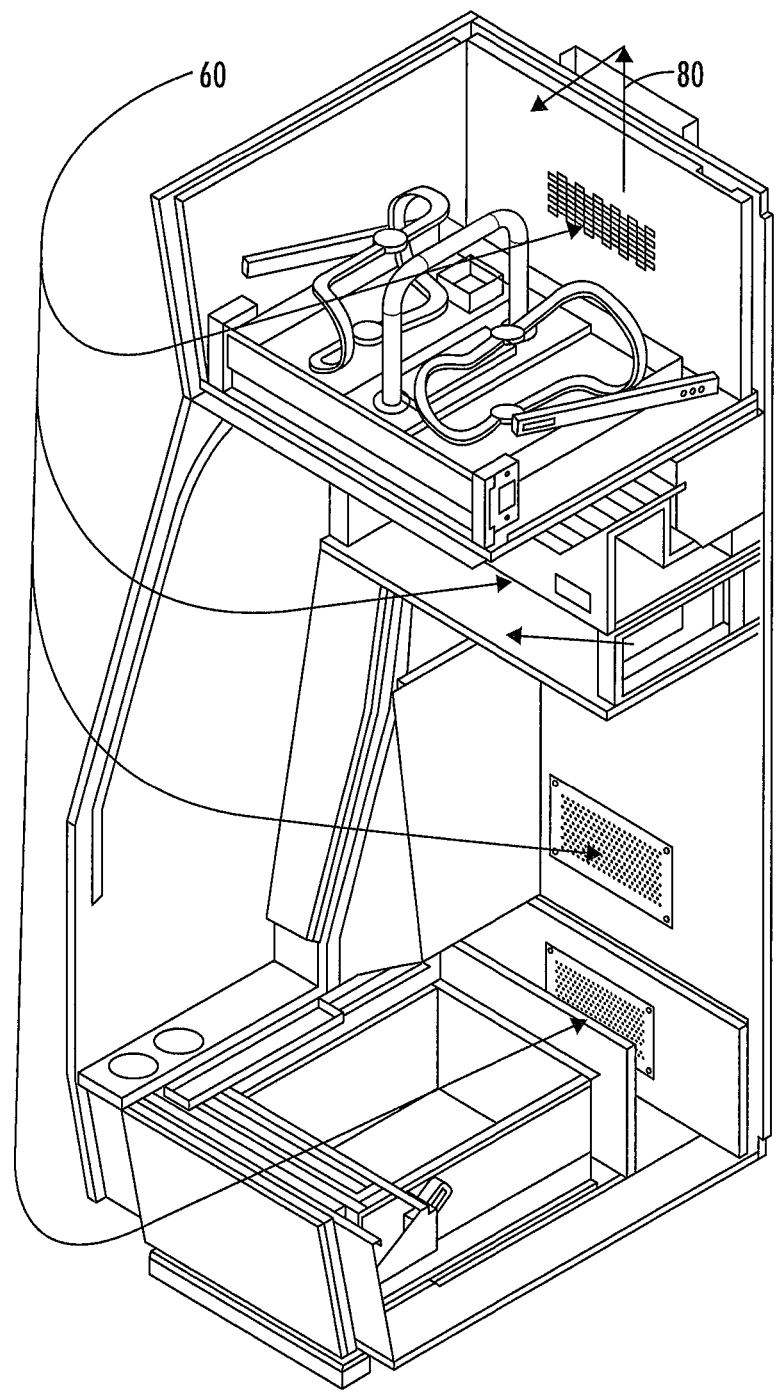
FIG. 8D is a perspective view of the locker of FIG. 3A, depicting chemical dispersion and dirty air flow according to the present application.

Referring now also to FIG. 8C in the drawings, a section view of the locker 71 is illustrated to depict ozone-integrated-air flow. Due to one or more re-circulating fans 78 disposed throughout the locker 71, the ozone-integrated-air is re-circulated to deodorize, decontaminate, and dissipate/remove bacteria and odors associated with equipment stored in the locker. More chemical pathways 79 are visible in the view depicted in FIGS. 8C and 8D, including a pathway for recirculated air 80.

It is noted that chemical dispensing units 63, 73 may increase and/or decrease in number depending on the size of the room in which the locker 61,71 is disposed. For example, a dispensing unit 63,73 may be configured to emit 10-100 milligrams per hour (mgph) of ozone to cover a 25-100 sq. ft. room, consuming 100 to 240 V (AC) of 50-60 Hz power.

When the locker is disposed in a room that is a factor of "X" larger and/or smaller than the 25-100 sq. ft. room, then the number of dispensing units 63,73 will correspondingly/linearly increase or decrease by the factor "X". It is noted, however, that the control for adjusting the chemical/ozone output of a single unit may not be linear, but are sometimes exponential, logarithmic, etc. Therefore, care is taken to calibrate the controls of an integrated chemical dispensing unit based on the desired chemical/ozone output at the time of installation.

It is further noted that the capacity, power, and output of the chemical dispensing units used for the lockers discussed herein are custom tailored to maintain a safe environment within a room in which they are installed. Installation and use instructions are provided with each unit installed. For example, a computer software package, a mobile app, or executable instructions, may be installed on a computer or a mobile device soon after purchase, including detailed instructions for appropriate use, maintenance, and/or installation. The detailed instructions may include calibration steps, setting activation times, establishing entry prevention times, how to enable automatic door locks, setting re-entry times, and other procedures for complying with federal regulations, directives, and municipal codes. The chemical dispensing units are used together with exhaust vents, HVAC, ductwork, and combinations thereof to form an air decontamination system for a locker and/or a locker room having a group of lockers installed therein.

EXAMPLES

Example 1

The chemical dispensing unit in a locker is an ozone generator, having a capacity of producing over 15,000 mgph (15 gph) of ozone. The ozone formation is accomplished by the dissociation of the bond between oxygen molecules and excitation of the oxygen molecules as found in O2.

Six ozone generators are operated for a period of four hours, with a maximum operation time of eight hours. The locker room remains unoccupied for a minimum period of four hours after operation of the ozone generators. The room in which the six ozone generators are installed is a 150 square foot room.

The room has 10-foot high walls. The volume of the room is 1,500 ft$^3$. Because this type of room requires a relatively high number of required air changes per hour, such as 15-21, the fans and/or HVAC system ventilating the room will have to be able to be configured to meet this requirement. The air change formula below, is used:

$$\text{RequiredCFM} = (\text{Volume of the room} \times \text{Air Changes per hour})/60 \text{ minutes} \quad (1)$$

Using the formula above, and a required air change per hour of 21, a required ventilation capacity is determined to be 525 CFM. This requirement is met by using 6-9 high-capacity fans, or fans rated at 80 CFM. It is noted that the air change requirement may also be met by incorporating the blower capacity of the HVAC into the Equation (1) above.

Example 2

The ozone generator is used in a truck saturated or partially saturated with residue and smell from cigarette smoke. The ozone generator is run for 30 minutes inside the truck. A period of two to four hours is given prior to reentry. Upon reentry, the smell is completely gone.

It is apparent that a system with significant advantages has been described and illustrated. The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description and claims. Although the present embodiments are shown above, they are not limited to just these embodiments, but are amenable to various changes and modifications without departing from the spirit thereof.

We claim:

1. A locker, comprising:
   a pair of spaced-apart upstanding sidewalls;
   at least one compartment defined between the pair of upstanding sidewalls and associated with upper and lower horizontal panels; and
   an integrated chemical unit for generating a chemical for odor removal disposed relative to at least one of:
   the at least one compartment;
   an upstanding sidewall;
   the upper horizontal panel; and
   the lower horizontal panel;
   an air and chemical diffuser in fluid communication with the integrated chemical unit;
   at least one integrated fan disposed over or between the pair of upstanding sidewalls; and
   an exhaust vent having one or more UV sources, catalyst sources, radicals, and combinations thereof;
   wherein the chemical for odor removal is ejected by the integrated chemical unit near the locker, thereby forming chemical-integrated air;
   wherein at least one of the upper and lower horizontal panels, the pair of spaced-apart upstanding sidewalls, and the at least one compartment are at least partially perforated so as to be in fluid communication with the integrated chemical unit; and
   wherein the integrated fan is configured to pull the chemical-integrated air into the locker, and to direct the chemical for odor removal and airflow through the integrated chemical unit, the air diffuser, and the partial perforations of the locker.

2. The locker according to claim 1, wherein at least one of the upper and lower horizontal panels are hollow and in fluid communication with the integrated fan, and serve as an air intake.

3. The locker according to claim 2, further comprising:
   an equipment rack.

4. The locker according to claim 3, wherein the equipment rack is perforated to receive the chemical for odor removal and airflow from the hollow horizontal panel to disperse the chemical for odor removal and airflow out of the perforations of the equipment rack.

5. The locker according to claim 1, further comprising:
   an induction fan.

6. The locker according to claim 5, further comprising:
   a plenum.

7. The locker according to claim 6, wherein the plenum is disposed along a rear panel of the locker relative to the induction fan and the integrated chemical unit to recirculate the chemical for odor removal and airflow throughout the locker.

8. The locker according to claim 1, wherein the locker is in fluid communication with an exhaust vent.

9. The locker according to claim 8, wherein the chemical for odor removal is directly removed from air around the locker using the exhaust vent prior to reentry into a locker room containing the locker.

10. The locker according to claim 1, further comprising:
a forced-air ventilation system;
wherein the forced-air ventilation system is in fluid communication with an HVAC system in a locker room.

11. The locker according to claim 1, wherein the integrated chemical unit is an ozone generator, the locker further comprising:
a control system for selectively controlling operational parameters including an amount of ozone generated by the ozone generator.

12. An air decontamination system for a locker, comprising:
a locker, comprising:
a pair of spaced-apart upstanding sidewalls;
at least one compartment defined between the pair of upstanding sidewalls and associated with upper and lower horizontal panels; and
an integrated chemical unit for generating a deodorizing chemical for odor removal disposed relative to the locker;
an air and chemical diffuser in fluid communication with the integrated chemical unit;
at least one integrated fan disposed over or between the pair of upstanding sidewalls; and
an exhaust vent having one or more UV sources, catalyst sources, radicals, and combinations;
wherein the chemical for odor removal is ejected by the integrated chemical unit near the locker, thereby forming chemical-integrated air;
wherein at least one of the upper and lower horizontal panels, the pair of spaced-apart upstanding sidewalls, and the at least one compartment are at least partially perforated so as to be in fluid communication with the integrated chemical unit;
wherein the integrated fan is configured to pull the chemical-integrated air into the locker, and to direct the chemical for odor removal and airflow through the integrated chemical unit, the air diffuser, and the partial perforations of the locker; and
wherein the chemical for odor removal and airflow exits a room associated with the locker through the exhaust vent.

13. The locker system according to claim 12, wherein at least one of the upper and lower horizontal panels are hollow and in fluid communication with the integrated fan, and serve as an air intake.

14. The locker system according to claim 13, wherein the locker further comprises:
an equipment rack.

15. The locker system according to claim 14, wherein the equipment rack is perforated to receive the chemical for odor removal and airflow from the hollow horizontal panel to disperse the chemical for odor removal and airflow out of the perforations of the equipment rack.

16. The locker system according to claim 12, further comprising:
one or more circulation fans.

17. The locker system according to claim 16, further comprising:
a plenum.

18. The locker system to claim 17, further comprising:
an induction fan;
wherein the plenum is disposed along a rear panel of the locker relative to the induction fan and the integrated chemical unit to recirculate the chemical for odor removal and airflow throughout the locker.

19. The locker system according to claim 12, wherein the chemical for odor removal is directly removed from air around the locker using the exhaust vent prior to reentry into the room associated with the locker system.

20. The locker system according to claim 12, further comprising:
a forced-air ventilation system;
wherein the forced-air ventilation system is in fluid communication with an HVAC system of a locker room; and
wherein the locker is disposed within the locker room.

* * * * *